United States Patent
Mosa et al.

(10) Patent No.: US 8,809,611 B2
(45) Date of Patent: Aug. 19, 2014

(54) METHOD FOR REMOVAL AND RECOVERY OF ORGANIC AMINES FROM A HYDROCARBON STREAM

(71) Applicant: Saudi Basic Industries Corporation, Riyadh (SA)

(72) Inventors: Fuad M. Mosa, Riyadh (SA); Shahid Majeed Azam, Riyadh (SA); Sultan Eid Al-Otaibi, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 14/070,039

(22) Filed: Nov. 1, 2013

(65) Prior Publication Data

US 2014/0148618 A1 May 29, 2014

Related U.S. Application Data

(63) Continuation of application No. PCT/EP2013/069932, filed on Sep. 25, 2013.

(30) Foreign Application Priority Data

Nov. 28, 2012 (EP) .................................... 12194658

(51) Int. Cl.
*C07C 7/00* (2006.01)
*C07C 209/86* (2006.01)
(52) U.S. Cl.
CPC .................................. *C07C 209/86* (2013.01)
USPC ........... 585/800; 585/502; 585/518; 585/520; 585/808; 585/809; 208/254 R
(58) Field of Classification Search
None
See application file for complete search history.

(56) References Cited

U.S. PATENT DOCUMENTS

| 2,263,176 | A |   | 11/1941 | Lazar et al. |   |
|---|---|---|---|---|---|
| 4,392,948 | A | * | 7/1983 | Debande | .................. 208/254 R |
| 5,811,619 | A |   | 9/1998 | Commereuc et al. |   |

FOREIGN PATENT DOCUMENTS

| EP | 2258674 | A1 | 8/2010 |
| GB | 2159140 | A | 5/1985 |
| GB | 2159140 |   | 11/1985 |
| WO | 2009095417 | A1 | 8/2009 |

OTHER PUBLICATIONS

European Search Report of the European Paten Office; European Application No. 12194658.6-1451; Dated Apr. 12, 2013; 35 pages.
International Search Report of the International Searching Authority for PCT/EP2013/069932 mailed Dec. 18, 2013, 5 pages.
Written Opinion of the International Searching Authority for PCT/EP2013/069932 mailed Dec. 18, 2013, 4 pages.

* cited by examiner

*Primary Examiner* — Sudhakar Katakam
(74) *Attorney, Agent, or Firm* — Cantor Colburn LLP

(57) ABSTRACT

A method for removal and recovery of an organic amine from a hydrocarbon stream containing the amine, including: i) mixing the hydrocarbon stream containing the amine with an aqueous inorganic acid in a volumetric ratio of hydrocarbon stream:aqueous inorganic acid of greater than 1:1-5:1, preferably 1.5:1-4:1, more preferably 3:1, ii) phase separating of hydrocarbon and aqueous phase; iii) removing the hydrocarbon phase and optionally further purifying thereof, iv) optionally recycling at least a part of the hydrocarbon phase obtained in step (iii) into mixing step (i), v) mixing the aqueous phase obtained in step (iii) with an aqueous alkaline solution, vi) phase separating of an aqueous phase and an organic phase formed, vii) removing the organic phase obtained in step (vi) and optionally further purifying thereof.

19 Claims, 1 Drawing Sheet

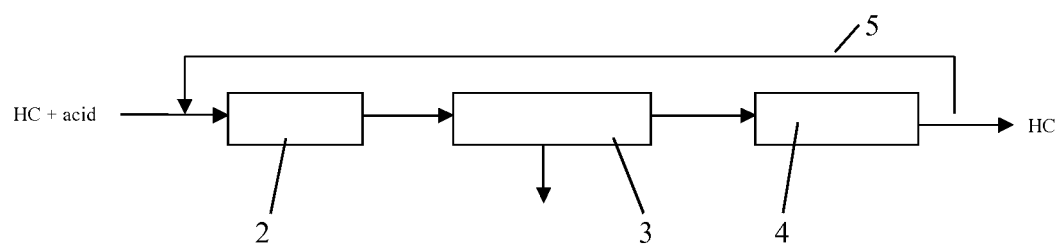

METHOD FOR REMOVAL AND RECOVERY OF ORGANIC AMINES FROM A HYDROCARBON STREAM

CROSS REFERENCE TO RELATED APPLICATIONS

This is a continuation of International Application No. PCT/EP2013/069932, filed Sep. 25, 2013, which claims priority to European Application No. 12 194 658.6, filed Nov. 28, 2012, both of which are hereby incorporated by reference in their entirety.

BACKGROUND

This application relates to a method for removal and recovery of an organic amine from a hydrocarbon stream.

In the chemical industry, processes are often conducted resulting in an outlet stream product or a feed stream to a process unit comprising hydrocarbon and amines. An example is the outlet stream from a reactor used for preparing linear alpha-olefins (LAOs) by oligomerization of ethylene. The linear alpha-olefins produced are then separated into different fractions for further use or marketing. Often, an amine is added during the oligomerization process or is added into a reactor outlet piping system. Such processes are, for example, disclosed in U.S. Pat. No. 5,811,619 or WO2009/095147. In other processes amines are used as corrosion inhibitors or for adjustment of a pH value.

In many cases, it is difficult to remove the organic amine from the hydrocarbon stream by distillation, because the boiling points of the amine and the hydrocarbon stream (or fractions thereof) are very close. For example, n-dodecylamine (DDA) is often added to oligomerization processes, which after product fractionation is carried through to the $C_{14}$-LAO product fraction. Since DDA has a boiling point close to the $C_{14}$-LAO product, it cannot readily be removed by distillation.

EP 2 258 674 A1 discloses a method for removal of an organic amine from a hydrocarbon stream comprising the steps of reacting the amine of the hydrocarbon stream containing the amine with an acid, optionally extracting the amine-salt formed into an aqueous phase, and optionally recovering and recycling of the amine. Using this method, the phase separation of organic and aqueous phases is time consuming, which is detrimental for industrial processes.

SUMMARY

It is therefore an object of the present invention to provide a method for removal and recovery of an organic amine from a hydrocarbon stream which overcomes the drawbacks of the prior art, especially to provide a method which allows easy and fast processing with quick phase separation of organic and aqueous phases.

In the method, removal and recovery of an organic amine from a hydrocarbon stream containing the amine comprises:

mixing the hydrocarbon stream containing the amine with an aqueous inorganic acid in a volumetric ratio of hydrocarbon stream:aqueous inorganic acid of greater than 1:1 to 5:1, phase separating of hydrocarbon and aqueous phase;

removing the hydrocarbon phase and optionally further purifying thereof, optionally recycling at least a part of the hydrocarbon phase obtained in step (iii) into mixing step (i), mixing the aqueous phase obtained in step (iii) with an aqueous alkaline solution, phase separating of an aqueous phase and an organic phase formed, removing the organic phase obtained in step (vi) and optionally further purifying the organic phase.

BRIEF DESCRIPTION OF THE FIGURE

The FIGURE is a schematic depiction of an exemplary process for the removal and recovery of an organic amine from a hydrocarbon stream containing the amine

DETAILED DESCRIPTION

This object is achieved by a method for removal and recovery of an organic amine from a hydrocarbon stream containing the amine, comprising the steps of: i) mixing the hydrocarbon stream containing the amine with an aqueous inorganic acid in a volumetric ratio of hydrocarbon stream: aqueous inorganic acid of greater than 1:1 to 5:1, preferably 1.5:1 to 4:1, more preferably 3:1, ii) phase separating of hydrocarbon and aqueous phase; iii) removing the hydrocarbon phase and optionally further purifying thereof, iv) optionally recycling at least a part of the hydrocarbon phase obtained in step (iii) into mixing step (i), v) mixing the aqueous phase obtained in step (iii) with an aqueous alkaline solution, vi) phase separating of an aqueous phase and an organic phase formed, vii) removing the organic phase obtained in step (vi) and optionally further purifying thereof.

It is preferred that the hydrocarbon stream containing the amine is an outlet stream from a reactor for preparing linear alpha-olefins (LAO) by oligomerization of ethylene or a fraction of such an outlet stream.

Preferably, the fraction is a product fraction in the range of $C_{10}$ to $C_{18}$.

It is most preferred that the aqueous inorganic acid is aqueous HCl in a concentration of 10 wt. %, preferably in a concentration of 5 wt. %, or aqueous sulfuric acid.

In a further embodiment, removal of the hydrocarbon phase in step (iii) is by decanting.

It is further advantageous that purification in step (iii) is by washing the hydrocarbon phase with water and passing the hydrocarbon phase obtained through an absorbing agent, the absorbing agent preferably being selected from the group of inorganic compounds, such as silica gel, alumina, and molecular sieve.

Further, it is proposed that purification of the organic phase in step (vii) is by washing with water, removing the aqueous phase and/or distilling any residual water from the organic phase.

In a preferred embodiment, the organic phase obtained in step (vii) is recycled into the hydrocarbon stream containing the amine before step (i). In a preferred embodiment, the amine is recycled into an oligomerization reactor or the reactor outlet stream thereof in order to scavenge chlorides formed therein to facilitate work-up of the oligomerization products obtained.

It is preferred that the aqueous phase obtained in step (vi) is transferred to a catalyst removal and deactivation section of a plant for oligomerization of ethylene. In a preferred embodiment, the volumetric ratio of organic phase and aqueous phase in step (vi) is preferably the same as given for step (i), i.e., an organic phase:aqueous phase of greater than 1:1 to 5:1, preferably 1.5:1 to 4:1, more preferably 3:1.

Finally, it is preferred that the pH in step (v) is basic.

Surprisingly, it was found that the inventive method for removal and recovery of an organic amine from a hydrocarbon stream provides finally a hydrocarbon product which can be marketed without any restriction due to its amine content. Further, the inventive method allows easy and actually complete removal of the amine from the hydrocarbon stream. Additionally, and most surprisingly, it was found that by adjusting the volumetric ratio when mixing the hydrocarbon stream containing the amine with an aqueous inorganic acid, phase separation can significantly be accelerated which results in benefits regarding processing time and costs involved. For a most preferred volumetric ratio of hydrocarbon to aqueous phases of 3:1 in step (i), a very short time period for achieving a clear phase separation is found. For example, the time required for a 3:1 volumetric ratio is about 4 times lower than the time of phase separation required for a 1:1 volumetric ratio. If at least a part of the hydrocarbon phase obtained in step (iii) is recycled into mixing step (i) this further improves complete solubilization of the inorganic amine and entering thereof into the aqueous phase as an amine salt.

Additionally, the costs for the amine utilized in respective chemical reaction processes can be considerably reduced, since the amine can be preferably recovered and recycled.

This is especially true for a method for preparing linear alpha-olefins, as disclosed above, wherein an organic amine is added into the oligomerization reaction and/or into the reactor outlet piping system. It was calculated that costs savings in an amount of several million Euro per year for a typical commercial plant for the oligomerization of ethylene can be achieved.

In a most preferred embodiment, the method for removal and recovery of an organic amine from a hydrocarbon stream containing the amine according to the invention is embedded in a method for preparing linear alpha-olefins by oligomerization of ethylene, preferably in the presence of solvents and catalyst, which comprises:
 a. feeding ethylene into an oligomerization reactor,
 b. oligomerizing the ethylene in the reactor,
 c. removing a reactor outlet stream comprising linear alpha-olefins from the reactor via a reactor outlet piping system,
 d. optionally transferring the reactor outlet stream to a catalyst deactivation and removal step, and
 e. optionally deactivating and removing the catalyst from the reactor outlet stream, wherein at least one organic amine is added into the oligomerization reactor and/or into the reactor outlet piping system. The reactor outlet stream or a fraction thereof can then be taken as the hydrocarbon stream in the present invention.

Additional features and advantages of the inventive method will now become apparent from the detailed description of embodiments thereof in conjunction with the drawings wherein the FIGURE shows a part of a schematic diagram of the inventive method. The FIGURE illustrates partly a schematic diagram of the inventive method with steps i)-iv).

According to the FIGURE, a hydrocarbon stream (HC) containing an amine and an aqueous inorganic acid, for example aqueous HCl, are provided at step 1 and are transferred to a mixing unit 2 were intimate mixing of the hydrocarbon stream and the aqueous inorganic acid is achieved. During the mixing, the amine in the amine containing hydrocarbon stream is reacted with the acid according to the following equation:

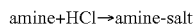

The amine salt is soluble in the aqueous phase and, as a consequence, can therefore be extracted from the hydrocarbon stream into the aqueous phase.

After mixing in the mixing unit 2, phase separation is initiated. This can be either done in the mixing unit itself when mixing has been terminated, or the mixture of hydrocarbon stream and aqueous phase can be transferred to a decanter unit 3. From the decanter unit 3, the aqueous phase can be separated and can be further processed according to steps v)-vii). The hydrocarbon phase can be also removed from the decanter unit 3 and can be transferred to a further purification unit 4 where the hydrocarbon stream can be washed with water (with an additional phase separation step), and the washed hydrocarbon stream can be passed through an absorbing agent to remove any water remained therein. Finally, a product hydrocarbon stream can be provided having less than 1 ppm of amine/amine salt and less than 1 ppm of acid.

At least a part of the purified hydrocarbon stream can then be preferably recycled into the mixing unit 2 via line 5 in order to adjust the appropriate volumetric ratio of hydrocarbon stream:aqueous inorganic acid in the mixing unit 2.

The aqueous phase obtained in step iii) can be further processed in order to recover and recycle the organic amine. For this purpose, the aqueous phase can be mixed with an aqueous alkaline solution, for example by realizing the following chemical equation:

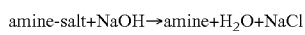

In this reaction step, the caustic (NaOH) can be also replaced by any other alkaline media, like $Ca(OH)_2$.

As the organic amine is soluble in water only to a limited extent, the organic amine will form a separate organic phase which can then be removed from the aqueous phase by phase separation. The organic phase containing the organic amine can then be further purified and can be, for example, washed with water with subsequent water removal steps, for example distillation.

The purified organic amine can then be re-used, for example, for dosing LAO reactor outlet lines or any oligomerization reactor.

In the reaction steps of the present invention, mixing elements, like static or dynamic mixers, may be utilized for optimizing the reaction efficiency. Further, after treatment with acid and caustic and separation of the amine from the hydrocarbon phase, the amine obtained can be washed with water several times to minimize the amount of entrained acid/caustic.

The different steps (reaction with acid, caustic or washing with water) can be performed in a once-through mode, or the reaction/washing efficiencies can be enhanced by installation of cycles.

EXAMPLES

For exemplarily illustrating the method for removal and recovery of any organic amine according to the present invention, a hydrocarbon stream containing solvent and $C_{10}$-$C_{18}$-olefins was provided. This hydrocarbon stream was mixed with an aqueous inorganic acid (HCl in a concentration of 10 wt. %) in the volumetric ratios as given below in table 1. The hydrocarbon stream and the aqueous inorganic acid were mixed for five seconds and the time for completing separation was measured. As can be taken from Table 1 below, best separation times are achieved for a volumetric ratio of hydrocarbon stream:aqueous inorganic acid of greater than 1:1.

TABLE 1

| LAO:inorganic acid (volumetric ratio) | Mixing time (seconds) | Complete separation time (seconds) |
|---|---|---|
| 1:3 (comparative) | 5 | 60 |
| 1:1 (comparative) | 5 | 80 |
| 5:3 | 5 | 25-30 |
| 3:1 | 5 | 20 |

The features disclosed in the foregoing description, in the claims and in the accompanying drawing may, both separately and in any combination thereof, be material for realizing the invention in diverse forms thereof.

What is claimed is:

1. A method for removal and recovery of an organic amine from a hydrocarbon stream containing the amine, comprising the steps of:
   i) mixing the hydrocarbon stream containing the amine with an aqueous inorganic acid in a volumetric ratio of hydrocarbon stream:aqueous inorganic acid of >1:1-5:1,
   ii) phase separating the hydrocarbon and the aqueous phase;
   iii) removing the hydrocarbon phase and optionally further purifying thereof,
   iv) optionally recycling at least a part of the hydrocarbon phase obtained in step (iii) into mixing step (i),
   v) mixing the aqueous phase obtained in step (iii) with an aqueous alkaline solution,
   vi) phase separating of an aqueous phase and an organic phase formed,
   vii) removing the organic phase obtained in step (vi) and optionally further purifying thereof.

2. The method according to claim 1, wherein the hydrocarbon stream containing the amine is an outlet stream from a reactor for preparing linear alpha-olefins (LAO) by oligomerization of ethylene or a fraction of such an outlet stream.

3. The method according to claim 2, wherein the fraction is a product fraction in the range of $C_{10}$ to $C_{18}$.

4. The method according to claim 1, wherein the aqueous inorganic acid is aqueous HCl or aqueous sulfuric acid.

5. The method according to claim 1, wherein removal of the hydrocarbon phase in step (iii) is by decanting.

6. The method according to claim 1, wherein further purification in step (iii) is by washing the hydrocarbon phase with water and passing the hydrocarbon phase obtained through an absorbing agent.

7. The method according to claim 1, wherein purification of the organic phase in step (vii) is by washing with water, removing the aqueous phase and/or distilling any residual water from the organic phase.

8. The method according to claim 1, wherein the organic phase obtained in step (vii) is recycled into the hydrocarbon stream containing the amine before step (i).

9. The method according to claim 1, wherein the aqueous phase obtained in step (vi) is transferred to a catalyst removal and deactivation section of a plant for oligomerization of ethylene.

10. The method according to claim 1, wherein the pH in step (v) is basic.

11. The method according to claim 1, wherein the volumetric ratio of hydrocarbon stream:aqueous inorganic acid is 1.5:1 to 4:1.

12. The method according to claim 11, wherein the volumetric ratio of hydrocarbon stream:aqueous inorganic acid is 3:1 to 5:1.

13. The method according to claim 12, wherein phase separation time in step (ii) is about four times lower than the time required for a 1:1 volumetric ratio.

14. A method for removal and recovery of an organic amine from a hydrocarbon stream containing the amine, comprising the steps of:
   i) mixing the hydrocarbon stream containing the amine with an aqueous inorganic acid in a volumetric ratio of hydrocarbon stream:aqueous inorganic acid of greater than 1:1 to 5:1,
   ii) phase separating of hydrocarbon and aqueous phase;
   iii) removing the hydrocarbon phase and optionally further purifying thereof,
   iv) optionally recycling at least a part of the hydrocarbon phase obtained in step (iii) into mixing step (i),
   v) mixing the aqueous phase obtained in step (iii) with an aqueous alkaline solution,
   vi) phase separating of an aqueous phase and an organic phase formed, wherein volumetric ratio of organic phase to aqueous phase is greater than 1:1 to 5:1,
   vii) removing the organic phase obtained in step (vi) and optionally further purifying thereof.

15. The method according to claim 14, wherein the volumetric ratio of organic phase to aqueous phase in step (vi) is 1.5:1 to 4:1.

16. The method according to claim 14, wherein the volumetric ratio of organic phase to aqueous phase in step (vi) is 3:1 to 5:1.

17. A method for removal and recovery of an organic amine from a hydrocarbon stream containing the amine, comprising the steps of:
   i) mixing the hydrocarbon stream containing the amine with an aqueous inorganic acid in a volumetric ratio of hydrocarbon stream:aqueous inorganic acid of greater than 1:1 to 5:1,
   ii) phase separating of hydrocarbon and aqueous phase;
   iii) removing the hydrocarbon phase and optionally further purifying thereof,
   iv) recycling at least a part of the hydrocarbon phase obtained in step (iii) into mixing step (i),
   v) mixing the aqueous phase obtained in step (iii) with an aqueous alkaline solution,
   vi) phase separating of an aqueous phase and an organic phase formed,
   vii) removing the organic phase obtained in step (vi) and optionally further purifying thereof.

18. The method according to claim 17, wherein the volumetric ratio of hydrocarbon stream:aqueous inorganic acid in step (i) is 1.5:1 to 5:1.

19. The method according to claim 17, wherein the volumetric ratio of hydrocarbon stream:aqueous inorganic acid in step (i) is 3:1 to 5:1.

* * * * *